United States Patent [19]

Foegh et al.

[11] Patent Number: 5,047,354
[45] Date of Patent: Sep. 10, 1991

[54] THROMBOXANE $B_2$ ASSAY FOR CORONARY ARTERY THROMBOSIS

[76] Inventors: Marie L. Foegh; Peter W. Ramwell, both of 1356 Kirby Rd., McLean, Va. 22101

[21] Appl. No.: 114,924

[22] Filed: Oct. 30, 1987

[51] Int. Cl.$^5$ .................. G01N 33/536; G01N 33/53; G01N 30/00
[52] U.S. Cl. .................................. 436/536; 436/501; 436/811; 436/815; 436/161; 435/7.1
[58] Field of Search ............... 436/536, 161, 808, 811, 436/815; 435/805, 810, 7

[56] References Cited

PUBLICATIONS

Foegh, M. L. et al., *Prostaglandins*, vol. 32, No. 5, pp. 781–788 (Nov. 1986).
Roberts, II, L. J. et al., *J. Biol. Chem.*, vol. 256, No. 16 (Aug. 25, 1981), pp. 8384–8393.
Viinikka, L. et al., Biological Abstracts, vol. 71, No. 7, p. 4658, Abstract No. 44465 (1981).
Hendriksson et al., *Br. Heart J.* 55:543–548 (1986).
Vesterqvist et al., *Thrombosis Research* 37:459–464 (1985).
FitzGerald et al., *Circulation* 67(6):1174–1176 (1983).
Foegh et al., *Lancet* 11:431–434 (1981).
Klotz et al., *Chest* 85:329–335 (1984).
Foegh et al., *Transplant. Proc.* 18, suppl. 4: (1986).
Zipser et al., *Gastroenterology* 84:697–703 (1983).
Zipser et al., *Prostaglandins* 27(2):257–271 (1984).
Strano et al., *Thromb Haemostas* 46:759 (1981).
Fitzgerald et al., *The New England Journal of Medicine* 315(16):983–989 (Oct. 16, 1986).

*Primary Examiner*—Esther L. Kepplinger
*Assistant Examiner*—Toni R. Scheiner
*Attorney, Agent, or Firm*—Sterne, Kessler, Goldstein & Fox

[57] ABSTRACT

This invention is directed to the use of thromboxane as an early indicator for coronary artery thrombosis (acute myocardial infarction), and assays for detecting thromboxane $B_2$ or a metabolite of $TXB_2$ or $TXA_2$.

5 Claims, 1 Drawing Sheet

THROMBOXANE $B_2$ ASSAY FOR CORONARY ARTERY THROMBOSIS

This invention was made using government funds. The United States government may have certain rights in this invention.

FIELD OF THE INVENTION

This invention is directed to the use of thromboxane $B_2$ or a metabolite of $TXB_2$ or $TXA_2$ as an early indicator for coronary artery thrombosis (acute myocardial infarction), and assays for detecting thromboxane $B_2$ or a metabolite of $TXB_2$ or $TXA_2$.

BACKGROUND OF THE INVENTION

Activation of blood components such as lymphocytes, granulocytes, monocytes, and platelets is associated with the release of thromboxane $A_2$ and other metabolites of arachidonic acid. Thromboxane $A_2$ ($TXA_2$) is formed from metabolism of arachidonic acid by the enzyme cyclooxygenase via cyclic endoperoxide intermediates. $TXA_2$, the major cyclooxygenase product in the platelet, is a vasoconstrictor and potent stimulus to platelet aggregation in vitro.

Platelets express a high synthetic capacity for thromboxane $A_2$ ($TXA_2$) and therefore this product may have clinical diagnostic significance. However, $TXA_2$ itself is chemically unstable with a half life of less than one minute. For this reason the stable breakdown product thromboxane $B_2$ ($TXB_2$) and its primary metabolite 2,3 dinor-$TXB_2$ are usually measured by RIA when large numbers of samples are required.

FitzGerald et al., "Analysis of Prostacyclin and Thromboxane Biosynthesis in Cardiovascular Disease," *Circulation* 67(6):1174 (1983) focuses on the methods that have been used for measuring prostacyclin and thromboxane $A_2$ in human biological fluids. After reviewing the difficulties associated with invasive analysis techniques for measuring prostacyclin and thromboxane $A_2$, the authors assert that the measurement of urinary metabolites represents the only noninvasive approach to quantitation of endogenous prostacyclin and thromboxane $A_2$ biosynthesis. In conclusion, the report states that further research is needed to define the relationship of tissue-specific, capacity-related indexes to endogenous production rates of prostacyclin and thromboxane $A_2$.

In thrombotic events such as deep vein thrombosis (Foegh et al., "Urine i-$TXB_2$ in Renal Allograft Rejection," *Lancet* II:431-434 (1981)) and pulmonary embolism (Klotz et al., "Urinary Excretion of Thromboxane $B_2$ in Patients with Venous Thromboembolic Disease," *Chest* 85:329-335 (1984)), and in renal and cardiac transplant rejection (Foegh et al., "Lipid Mediators in Organ Transplantation," *Transplant. Proc.* 18, *suppl.* 4: (1986)), the urinary excretion of immunoreactive-$TXB_2$ (i-$TXB_2$) which includes 2,3 dinor $TXB_2$, is significantly increased.

For illustration, in Foegh et al., *Lancet, supra* report that not only may urinary i-$TXB_2$ be a predictor of clinical renal allograft rejection, it may also be a used in the early diagnosis of venous thrombosis. Klotz et al., *Chest, supra,* studied the use of urinary i-$TXB_2$ as an indication of platelet activation and as a possible adjunct for diagnosing acute thromboembolic disease.

Coronary artery thrombosis, which may lead to acute myocardial infarction, is another thrombotic event where an increase in thromboxane formation might be anticipated. Attempts to measure plasma values are not entirely satisfactory owing to the large potential for sampling artefacts. (Granstrom et al., "The Thromboxanes," in *Prostaglandins and Related Substances*, (C. Pace-Asciak and E. Granstrom eds.), Elsevier, Amsterdam (1983), p. 45) Urinary i-$TXB_2$ determinations provides a means of avoiding such artefacts but whether infarction is associated with a rise in urinary i-$TXB_2$ is not known.

SUMMARY OF THE INVENTION

This invention is directed to the use of thromboxane $B_2$ or a metabolite of $TXB_2$ or $TXA_2$ as an early indicator for coronary artery thrombosis (acute myocardial infarction), and assays for detecting thromboxane $B_2$ or a metabolite of $TXB_2$ or $TXA_2$.

DETAILED DESCRIPTION OF THE INVENTION

Figure 2:
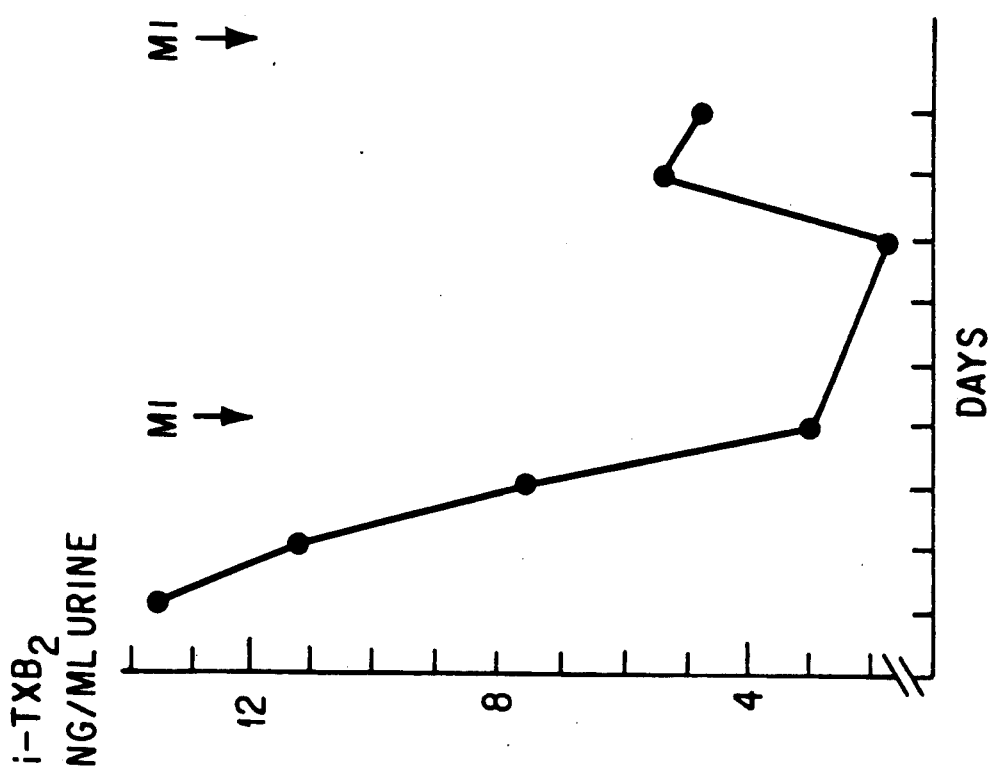
FIG. 2 shows daily immunoreactive thromboxane $B_2$ (i-$TXB_2$) in a 61-year-old kidney transplant patient from 3 days prior to the first myocardial infarction and until one day prior to the second and fatal myocardial infarction. This observation strongly indicates that measurement of urine i-$TXB_2$ is capable of detecting on-going coronary thrombosis at a time when damage to the myocardium (myocardial infarct) has not yet occurred.

Thromboxane $B_2$ has been shown to be of use for the diagnosis of renal allograft rejection (M. L. Foegh et al., "Urine i-$TXB_2$ in Renal Allograft rejection," *Lancet* ii:431 (Aug. 81)) and deep venous thrombosis (T. A. Klotz et al., "Urinary Excretion of Thromboxane $B_2$ in Patients with Venous Thromboembolic Disease," *Chest* 85(3):329 (Mar. 84)). In Klotz et al., the authors also tested patients with coronary thrombosis, but were unable to show any significant increase in thromboxane levels in such patients. The accepted explanation for this has been that the thrombus developed in that case are rather small compared to the thrombus that are developed in venous thromboembolic diseases.

The fact that Klotz et al. were unable to show any difference between thromboxane $B_2$ levels in patients suffering from myocardial infarction or angina pectoris indicated that thromboxane could not be used as an early indicator for infarction, and consequently the onset of treatment with the proper thrombolytic agent had to be postponed, which entailed an increased risk for the patient.

It is believed that approximately 50% of those patients who die from an infarction could be saved if an early indication would allow for an early onset of the proper treatment. Especially for people who are susceptible to thrombic events, this assay described and claimed herein is of great importance.

This invention is therefore directed to an assay for measuring for the presence of thromboxane $B_2$ or a metabolite of $TXB_2$ or $TXA_2$ in a sample from a patient suspected of having coronary artery thrombosis or a myocardial infarction. As used herein the measurement of thromboxane $B_2$ may also include the measurement of metabolites of thromboxane $B_2$, such as 2,3-dinor $TXB_2$ or 11-dehydro-$TXB_2$, and other known metabolites. This invention is also meant to include other metabolites of $TXA_2$ which can be measured. In this invention, the measurement of thromboxane $B_2$ is also meant to mean the measurement one or more of the metabolites of thromboxane $B_2$ alone, such as the measurement of 2,3-dinor $TXB_2$ or 11-dehydro-$TXB_2$, or the measurement of one or more of the metabolites of thromboxane $A_2$ alone.

Coronary artery thrombosis is generally a physiologic event resulting from a thrombus in the coronary artery. Coronary artery thrombosis can lead to acute myocardial infarction which is defined as an area of necrosis in the heart tissue resulting from obstruction of the local circulation by a thrombus or embolus. Pain is frequently associated with myocardial infarction, however, other heart ailments are also associated with pain but not with thrombus, such as angina.

The assay of this invention involves the measurement of thromboxane $B_2$ using methods known in the art, such as gas chromatography/mass spectrography (GC/MS) or radioimmunoassay (RIA). Other immunoassays may also be used including immunometric assays, such as forward sandwich immunoassays, reverse sandwich immunoassays, and simultaneous assays, and competitive assays.

With the immunometric assays, and the radioimmunoassay, a high titer antibody is used that is specific against $TXB_2$, or a metabolite of $TXB_2$, such as 2,3-dinor $TXB_2$ or 11-dehydro-$TXB_2$, or a metabolite of $TXA_2$. The antibody can be either monoclonal antibody or polyclonal antibody.

The sample to be tested for coronary artery thrombosis may any biological sample in which $TXB_2$ can be measured. Typically the sample will be blood, plasma, serum, or urine.

The urine sample collected from the patients may be extracted or purified prior to the assay. If an immunometric or RIA is performed, the thromboxane in the urine sample may be measured by direct assay without extraction. Typically, however, the urine will be extracted either by centrifugation alone, or the sample can be collected and mixed with indomethacin at 10-20 ug/ml urine and then centrifuged. The indomethacin does not interfere with the assay of i-$TXB_2$. If a GC/MS assay is used, the urine sample is first purified using known means in the art.

The immunoassays in the method of the invention are ideally suited for preparation of a kit. Such a kit may comprise a carrier means being compartmentalized to receive in close confinement one or more container means such as vials, tubes, and the like, each of said container means comprising the separate elements of the immunoassay. For example, there may be a container means containing the first antibody immobilized on a solid phase support, and further container means containing detectably labeled titrating antibodies either lyophilized or in solution.

Further container means may contain standard solutions comprising serial dilutions of thromboxane $B_2$ to be detected. The standard solutions may be used to prepare a standard curve with the concentration of the thromboxane $B_2$ plotted on the abscissa and the detection signal on the ordinate. The results obtained from a urine sample containing thromboxane $B_2$ may be interpolated from such a plot to give the concentration.

In another embodiment of the kit, there may be a container means containing a dipstick which comprises a thromboxane $B_2$ antibodies immobilized to a defined area of the solid phase support. Further container means may contain a common titrating antibody which is specific for the thromboxane $B_2$ antibody. Further container means may contain standard solutions of thromboxane $B_2$ to be detected. The standard solutions of the thromboxane $B_2$ may be used to provide a standard reference dipstick for comparison with the sample dipstick.

Thus, this invention is directed to the use of thromboxane $B_2$, and/or its metabolites, and/or the metabolites of thromboxane $A_2$ as an early indicator for coronary artery thrombosis prior to acute myocardial infarction. Further, this invention is directed to the use of thromboxane $B_2$, and/or its metabolites, and/or the metabolites of thromboxane $A_2$ in detecting acute myocardial infarction. For example, the assay, in kit form, may be performed by a patient in order to monitor his or her situation. Such assays will put the patient and/or physician in a better position to select a suitable treatment, such as by prescribing thrombolytic agents, at an early stage, and preferably prior to the infarction. Nonsteroidal anti-inflammatory drugs, such as aspirin, inhibit the cyclooxygenase enzyme such that thromboxane $A_2$ is not formed from the metabolism of arachidonic acid. Thus, the use of aspirin must be documented to have an accurate measurement of thromboxane according to this invention. If nonsteroidal anti-inflammatory drugs have been used by a patient prior to the assay of this invention, then repeat testing is generally warranted.

Having generally described the invention, further understanding can be obtained by reference to certain specific examples which are provided herein for purposes of illustration only and are not intended to be limiting unless otherwise specified.

EXAMPLES

Immunoreactive thromboxane $B_2$ (i-$TXB_2$) was measured by radio-immunoassay (RIA) in urine collected over eight hours on the day of admission in 25 patients who were admitted with the diagnosis of myocardial infarction. In 16 of the patients, myocardial infarction was confirmed by ECG and plasma enzymes. Another patient presented with pulmonary embolism and the remaining eight patients had angina pectoris. A further eight hour urine collection was obtained 24 hours later from eleven of the sixteen patients with myocardial infarction. In these eleven patients myocardial infarction was associated with five fold higher urine i-$TXB_2$ (2.72 $\pm$0.48 ng/ml) at the day of admission when compared to patients admitted under the same diagnosis but found to have angina only (0.51$\pm$0.08 ng/ml, p<0.001). In patients with myocardial infarction the urine i-$TXB_2$ values were reduced 24 hours later (1.58$\pm$0.27 ng/ml, p <0.01). One patient was followed with urine i-$TXB_2$ from three days prior to diagnosis of myocardial infarction and to one day prior to a second infarction. In this patient i-$TXB_2$ was highest three days prior to infarction. We conclude that this early elevation of urine i-$TXB_2$ three days prior to diagnosis of infarction and the increased i-$TXB_2$ in patients with myocardial infarction when compared to patients with angina suggest thromboxane is probably released from activated platelets prior to infarction. Thus, the measurement of urine i-TXB$_2$ is of value in the differential diagnosis between coronary artery thrombosis and early myocardial infarction on the one hand and angina pectoris not caused by thrombotic events on the other hand.

PATIENTS AND METHODS

Twenty-five patients aged 45 to 86 years old (average 63) were admitted to the intensive cardiac care unit at the Herley Hospital with anginal pain and possible myocardial infarction. Urine were collected during an eight-hour period for urine i-TXB$_2$ determination by RIA. Sixteen patients had myocardial infarction diagnosed by electrocardiogram and serum enzymes (lactic dehydrogenase and aspartate transferase). Eleven of the 16 patients had in addition i-TXB$_2$ determined in an eight-hour urine sample which was collected 24 hours later. One patient had pulmonary embolism, and the remaining patients had angina but not myocardial infarction. Two patients from the group with myocardial infarction were excluded due to extremely low urine i-TXB$_2$ concentrations in the range which occurs following ingestion of aspirin (Fitzgerald et al., "Endogenous biosynthesis of prostacyclin and thromboxane and platelet function during chronic administration of aspirin in man," *J. Clin. Invest.* 71:676-688 (1983)), although the medical history did not indicate this. At Georgetown University Hospital a renal transplant patient who developed myocardial infarction was admitted for pneumonia three months after transplantation. He was followed with urinary i-TXB$_2$ which is a routine procedure for the renal transplant patients.

The urine were collected and mixed with indomethacin, centrifuged and an aliquot was stored at $-20°$ C. Urine i-TXB$_2$ was determined by radio-immunoassay as previously described with the widely used antibody of Dr. L. Levine of Brandeis University, Mass. (Foegh et al., *Lancet* II:431-434 (1981)). This is a high titer TXB$_2$ antibody which cross-reacts 60% with the major metabolite in urine of TXA$_2$, namely 2,3-dinor TXB$_2$ (Roberts et al., "Metabolism of thromboxane B$_2$ in man: Identification of twenty urinary metabolites," *J. Biol. Chem.* 256:8384-8393 (1981)). Urinary determinations made by direct RIA with the same antibody as used here, was found to correlate with urinary 2,3-dinor TXB$_2$ as determined by gas chromatography, mass spectrometry in patients with deep vein thrombosis and pulmonary embolism (Zipser et al., "Urinary thromboxane B$_2$ and prostaglandin E$_2$ in the hepatorenal syndrome: evidence or increased vasoconstrictor and decreased vasodilator factors," *Gastroenterology* 84:697-703 (1983)). Previous studies have demonstrated that urinary i-TXB$_2$ excretion is influenced by urinary flow rate, such that the concentration of i-TXB$_2$ tends to remain constant during different rates of urine flow (Zipser et al., "Regulation of urinary thromboxane B$_2$ in man: influence of urinary flow rate and tubular transport," *Prostaglandins* 87:1228-1232 (1984)), consequently urinary i-TXB$_2$ is expressed as ng/ml, since fluid intake was not regulated.

RESULTS

Figure 1:
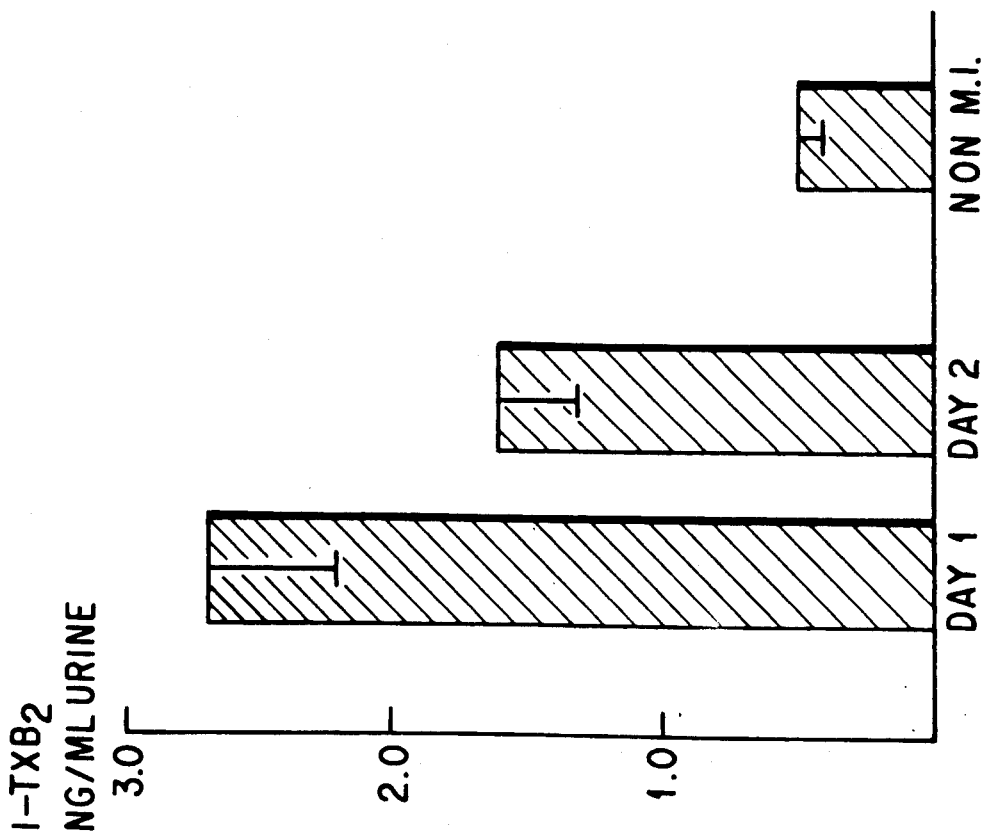
FIG. 1 shows immunoreactive thromboxane $B_2$ (i-$TXB_2$) values in urine (ng/ml) in 16 patients with angina and myocardial infarction (M.I.) on the day of admission to the hospital (day 1) and the following day (day 2). Non M.I. represents the urine i-$TXB_2$ on the admission day in patients admitted for myocardial infarction, but where the diagnosis was ruled out by ECG and serum enzyme changes.

The diagnosis of myocardial infarction was based on ECG and plasma enzyme changes in all cases. Sixteen of the 25 patients had myocardial infarction, but two were excluded due to extremely low urinary i-TXB$_2$ (<0.09 ng/ml urine) which was characteristic of aspirin ingestion. A statistical significant difference was found between urine i-TXB$_2$ in patients with myocardial infarction ($2.72 \pm 0.48$ ng/ml) and in patients with angina without infarction ($0.51 \pm 0.08$ ng/ml; $p < 0.001$). In eight-hour urine samples which were collected 24 hours later from the group with myocardial infarction, the urinary i-TXB$_2$ values decreased to $1.58 \pm 0.27$ ng/ml. These values were still significantly higher ($p < 0.05$) than those from patients with angina only (FIG. 1). Three patients died due to myocardial infarction; however, the urine i-TXB$_2$ level was not higher than in the patients surviving the episode. No correlation was found between urine i-TXB$_2$ and serum lactate dehydrogenase or aspartate transferase in the patients with myocardial infarction. The medication prior to admission was similar in patients with and without myocardial infarction (Table I). During the stay in the intensive cardiac care unit the patients continued their usual medication; in addition, digoxin and furosemide were initiated in 3 and 5 patients, respectively, with myocardial infarction.

TABLE I

Drugs administered to patients, before admission to the cardiac intensive care unit, who developed infarction (+M.I.) and those who did not (−M.I.). The drugs were continued after admission.

| DRUG | +M.I. | −M.I. |
|---|---|---|
| NITROGLYCERINE | 2 | 1 |
| THIAZIDE | 5 | 1 |
| FUROSEMIDE | 4 | 4 |
| DIGOXIN | 3 | 3 |
| BETA-BLOCKERS | 4 | 1 |
| Ca$^{++}$ BLOCKERS | 1 | 0 |
| LIDOCAINE | 0 | 1 |
| INSULIN | 2 | 1 |

The renal transplant patient admitted with pneumonia who was routinely followed with daily urine i-TXB$_2$ exhibited elevated values three days prior to diagnosis of myocardial infarction, after which the values decreased. On the day of angina and the diagnosis of myocardial infarction by ECG and characteristic enzyme changes, the i-TXB$_2$ value was approximately the same (3.01 ng/ml) as that measured in the patients admitted with myocardial infarction ($2.72 \pm 0.48$ ng/ml). The urine i-TXB$_2$ value of this transplant patient continued to decrease after the diagnosis of myocardial infarction as seen in the patients with myocardial infarction from the Herlev Hospital. A second rise in urine i-TXB$_2$ occurred four days later and the patient died the following day from a second myocardial infarction (FIG. 2).

DISCUSSION

Urine i-TXB$_2$ values were significantly elevated five to six fold on the day of acute admission of patients subsequently proven to have myocardial infarction, when compared to the patients only presenting with angina only. The urine i-TXB$_2$ values subsequently decreased the following day and approached the values measured in patients with angina only. The data from the renal transplant patient who had two consecutive infarcts suggest that urine i-TXB$_2$ increases prior to the development of myocardial infarction. The i-TXB$_2$ values are elevated at the time of diagnosis and decrease over subsequent days as seen with the patients at the Herlev Hospital. The case of the renal transplant patient was noteworthy in that the second myocardial infarction was also preceded by a second increase in urine i-TXB$_2$.

In renal transplant patients urinary i-TXB$_2$ is increased prior to the clinical diagnosis of rejection Foegh et al., *Lancet, supra.*; the i-TXB$_2$ values observed are lower than those seen in the kidney transplant patient with myocardial infarction. Moreover, clinically the patient was not undergoing a rejection episode by standard criteria. The patient was admitted with pneumonia which does not elevate urinary i-TXB$_2$ Foegh et al., *Lancet, supra.* Finally, urine i-TXB$_2$ is not increased with a decline in kidney function. On the other hand, elevated urinary i-TXB$_2$ of this magnitude may be due to deep vein thrombosis (Foegh et al., *Lancet, supra.*; Klotz et al., *Chest, supra.*) but this was not the case. We conclude that the two elevated urinary i-TXB$_2$ values in this patient were associated with the two infarction episodes. This observation strongly indicates that measurement of urine i-TXB$_2$ is capable of detecting ongoing coronary thrombosis at a time when damage to the myocardium (myocardial infarct) has not yet occurred.

Plasma TXB$_2$ is reported to be detectable on the day of myocardial infarction in a group of 10 patients Strano et al., *Thromb Haemostas* 46:759 (1981). This observation is in accordance with the increase in urine i-TXB$_2$ seen in our patients with myocardial infarction. Thus, elevated urinary i-TXB$_2$ is useful in the differential diagnosis of angina and angina associated with coronary artery thrombosis or myocardial infarction. The increase in urine i-TXB$_2$ which occurred 3 days prior to coronary thrombosis is similar to the increase previously reported 5 days prior to diagnosis of deep vein thrombosis Foegh et al., *Lancet. supra.* Furthermore, urine i-TXB$_2$ values measured prior to coronary thrombosis was of the same magnitude as seen prior to deep vein thrombosis. This suggests that a general activation of platelets may take place. The observation that urine i-TXB$_2$ is elevated prior to diagnosis of myocardial infarction should make intervention more effective.

In summary, patients with myocardial infarction exhibit significantly higher values of urine i-TXB$_2$ than patients with angina. The urinary i-TXB$_2$ decreases rapidly 24 hours after diagnosis. A case history suggests that urine i-TXB$_2$ may increase several days prior to the myocardial infarction at the time when the thrombus may be only in cardiac formation. Urinary i-TXB$_2$ may help to differentiate between angina alone and angina associated with coronary thrombosis or myocardial infarction.

Although the foregoing invention has been fully described by way of illustration and example for purposes of clarity and understanding, it will be obvious that certain changes and modifications may be practiced within the scope of the invention, as limited only by the scope of the appended claims.

What is claimed is:

1. A method for detecting coronary artery thrombosis before a myocardial infarction in a patient comprising:
    (a) obtaining a sample from a patient susceptible to having coronary artery thrombosis;
    (b) determining levels of thromboxane B$_2$ (TXB$_2$) or a metabolite of TXB$_2$ or thromboxane A$_2$ (TXA$_2$) in said sample; and
    (c) diagnosing a coronary artery thrombosis based upon comparison of the levels of TXB$_2$ or a metabolite of TXB$_2$ or TXA$_2$ in said sample with normal levels, wherein an elevated level is diagnostic of an impending infarction.

2. The method of claim 1 wherein said TXB$_2$ or metabolite of TXB$_2$ or metabolite of TXA$_2$ is measured using an immunoassay.

3. The method of claim 1 wherein said TXB$_2$ or metabolite of TXB$_2$ or metabolite of TXA$_2$ is measured using gas chromatography/mass spectrography.

4. The method of claim 1 wherein the sample is blood, plasma, serum, or urine.

5. The method of claim 1 wherein said metabolite of TXB$_2$ is 2,3 dinor TXB$_2$ or 11-dehydro TXB$_2$.

* * * * *